United States Patent
Li et al.

(10) Patent No.: US 11,033,187 B2
(45) Date of Patent: Jun. 15, 2021

(54) TEXT TO BRAILLE CONVERTER

(71) Applicants: Grace Li, Cambridge, MA (US); Chen Wang, Cambridge, MA (US); Chandani Doshi, Cambridge, MA (US); Tania Yu, Cambridge, MA (US); Jialin Shi, Cambridge, MA (US); Charlene Xia, Cambridge, MA (US)

(72) Inventors: Grace Li, Cambridge, MA (US); Chen Wang, Cambridge, MA (US); Chandani Doshi, Cambridge, MA (US); Tania Yu, Cambridge, MA (US); Jialin Shi, Cambridge, MA (US); Charlene Xia, Cambridge, MA (US)

( * ) Notice: Subject to any disclaimer, the term of this patent is extended or adjusted under 35 U.S.C. 154(b) by 113 days.

(21) Appl. No.: 15/374,398

(22) Filed: Dec. 9, 2016

(65) Prior Publication Data

US 2018/0082609 A1 Mar. 22, 2018

(30) Foreign Application Priority Data

Sep. 16, 2016 (IN) .............................. 201641031606

(51) Int. Cl.
| | |
|---|---|
| *A61B 5/00* | (2006.01) |
| *G09B 21/00* | (2006.01) |
| *G06K 9/20* | (2006.01) |
| *G06K 9/36* | (2006.01) |
| *G06K 9/78* | (2006.01) |

(Continued)

(52) U.S. Cl.
CPC ............. *A61B 5/0022* (2013.01); *A61B 1/05* (2013.01); *A61B 5/0205* (2013.01); *A61B 5/14535* (2013.01); *A61B 5/14551* (2013.01); *A61B 5/30* (2021.01); *A61B 5/7445* (2013.01); *A61B 7/04* (2013.01); *G06K 9/209* (2013.01); *G06K 9/344* (2013.01); *G06K 9/36* (2013.01); *G06K 9/78* (2013.01); *G09B 21/003* (2013.01); *G16H 10/60* (2018.01); *G16H 50/20* (2018.01); *A61B 2562/22* (2013.01); *G06K 2209/01* (2013.01)

(58) Field of Classification Search
CPC ................................. G06K 9/344; G06K 9/78
See application file for complete search history.

(56) References Cited

U.S. PATENT DOCUMENTS

| | | | | |
|---|---|---|---|---|
| 6,115,482 | A * | 9/2000 | Sears | G06F 3/011 348/62 |
| 6,970,591 | B1 * | 11/2005 | Lyons | G06K 9/209 345/419 |

(Continued)

FOREIGN PATENT DOCUMENTS

EP     2096614 B1    11/2015

OTHER PUBLICATIONS

"Office Action Issued in Indian Patent Application No. 201641031606", dated May 21, 2020, 6 Pages.

*Primary Examiner* — Jerry-Daryl Fletcher
*Assistant Examiner* — Sadaruz Zaman

(57) ABSTRACT

A text-to-Braille service is disclosed herein that includes an imaging module. The imaging module includes multiple cameras arranged to image part of a page of text. Each camera has a different field of view of the page, so each camera images a unique portion of the page. The multiple images can be combined to form a single image upon which optical character recognition is performed. The text of the page can be converted into Braille characters and displayed on a refreshable Braille device.

13 Claims, 9 Drawing Sheets

(51) Int. Cl.
*G06K 9/34* (2006.01)
*A61B 5/30* (2021.01)
*G16H 10/60* (2018.01)
*G16H 50/20* (2018.01)
*A61B 1/05* (2006.01)
*A61B 5/0205* (2006.01)
*A61B 5/145* (2006.01)
*A61B 5/1455* (2006.01)
*A61B 7/04* (2006.01)

(56) References Cited

U.S. PATENT DOCUMENTS

| | | | |
|---|---|---|---|
| 9,875,670 B2* | 1/2018 | Al-Salman | B41J 3/32 |
| 9,965,974 B2* | 5/2018 | Labbe | G09B 21/004 |
| 10,395,555 B2* | 8/2019 | Djugash | G09B 21/006 |
| 10,528,833 B1* | 1/2020 | Bhatnagar | A61B 5/1118 |
| 2006/0029296 A1* | 2/2006 | King | H04N 1/00244 |
| | | | 382/313 |
| 2006/0098899 A1* | 5/2006 | King | G06F 17/218 |
| | | | 382/305 |
| 2006/0187305 A1* | 8/2006 | Trivedi | G06K 9/00241 |
| | | | 348/169 |
| 2007/0230748 A1* | 10/2007 | Foss | G10L 13/00 |
| | | | 382/114 |
| 2008/0162474 A1* | 7/2008 | Thong | G06F 16/532 |
| 2009/0035731 A1* | 2/2009 | Murphy | G09B 21/003 |
| | | | 434/114 |
| 2014/0120981 A1* | 5/2014 | King | H04N 1/00334 |
| | | | 455/556.1 |
| 2014/0132708 A1* | 5/2014 | Kato | G06T 3/4038 |
| | | | 348/36 |
| 2014/0306814 A1* | 10/2014 | Ricci | B60Q 9/00 |
| | | | 340/425.5 |
| 2014/0314338 A1* | 10/2014 | Hamel | G06K 9/344 |
| | | | 382/321 |
| 2015/0123816 A1* | 5/2015 | Breed | G08G 1/096783 |
| | | | 340/905 |
| 2015/0154885 A1* | 6/2015 | Livermore-Clifford | |
| | | | G09B 21/003 |
| | | | 434/114 |
| 2015/0199566 A1* | 7/2015 | Moore | G06K 9/00442 |
| | | | 348/47 |
| 2015/0262509 A1* | 9/2015 | Labbe | G09B 21/004 |
| | | | 434/113 |
| 2016/0148538 A1* | 5/2016 | Al-Busaidi | G09B 21/003 |
| | | | 434/114 |
| 2016/0232817 A1* | 8/2016 | Djugash | G09B 21/02 |
| 2016/0234437 A1* | 8/2016 | Kuwada | H04N 5/23238 |
| 2018/0033336 A1* | 2/2018 | Shah | G09B 21/007 |

* cited by examiner

TEXT TO BRAILLE CONVERTER

TECHNICAL BACKGROUND

Braille is a tactile writing system used by people who are blind or visually impaired. It is traditionally written with embossed paper. Braille characters are small rectangular blocks called cells that contain tiny palpable bumps called raised dots. The number and arrangement of these dots distinguish one character from another. A full Braille cell includes six raised dots arranged in two lateral rows each having three dots. The dot positions are identified by numbers from one through six. 64 solutions are possible from using one or more dots. A single cell can be used to represent an alphabet letter, number, punctuation mark, or even an entire word. An increase in the availability of screen-reader software has caused Braille usage to declined. However, early Braille education is crucial to literacy for a blind or low vision child. A study conducted in the state of Washington in the United States of America found that people who learned Braille at an early age did just as well, if not better, than their sighted peers in several areas, including vocabulary and comprehension. In a preliminary adult study, while evaluating the correlation between adult literacy skills and employment, it was found that 44 percent of the participants who had learned to read in Braille were unemployed, compared to the 77 percent unemployment rate of those who had learned to read using print.

Unfortunately, less than one percent of all texts have a Braille translation. An audio translation of a text is not a literacy translation and does not provide the same benefits. This lack of access to printed texts is a disadvantage for the visually impaired.

Braille-users can read computer screens and other electronic supports using a refreshable Braille displays. A refreshable Braille display (also known as a Braille terminal) is an electro-mechanical device for displaying Braille characters, usually by means of round-tipped pins raised through holes in a flat surface. Blind or visually impaired computer users who cannot use a computer monitor can use it to read text output. The software that controls the refreshable Braille display is most commonly a screen reader. The screen reader gathers the content of a computer screen from the operating system, converts it into Braille characters and sends it to the refreshable Braille display. While such a system is useful for reading text on a computer, refreshable Braille displays coupled to screen readers do not enable paper books to be read.

Overview

A text-to-Braille service is disclosed herein that includes an imaging module. The imaging module includes multiple cameras arranged to image each part of a page of text. Each camera has a different field of view of the page, so each camera images a unique portion of the page. The multiple images can be combined to form a single image upon which optical character recognition is performed. The text of the page can be converted into Braille characters and displayed on a refreshable Braille display. The impact of invention is to give visually impaired people more opportunity and independence in their everyday life by providing the opportunity to read printed texts that are not available in a form readable for those who are visually impaired.

This Overview is provided to introduce a selection of concepts in a simplified form that are further described below in the Technical Disclosure. It may be understood that this Overview is not intended to identify key features or essential features of the claimed subject matter, nor is it intended to be used to limit the scope of the claimed subject matter.

BRIEF DESCRIPTION OF THE DRAWINGS

Many aspects of the disclosure can be better understood with reference to the following drawings. While several implementations are described in connection with these drawings, the disclosure is not limited to the implementations disclosed herein. On the contrary, the intent is to cover all alternatives, modifications, and equivalents.

TECHNICAL DISCLOSURE

Figure 1:
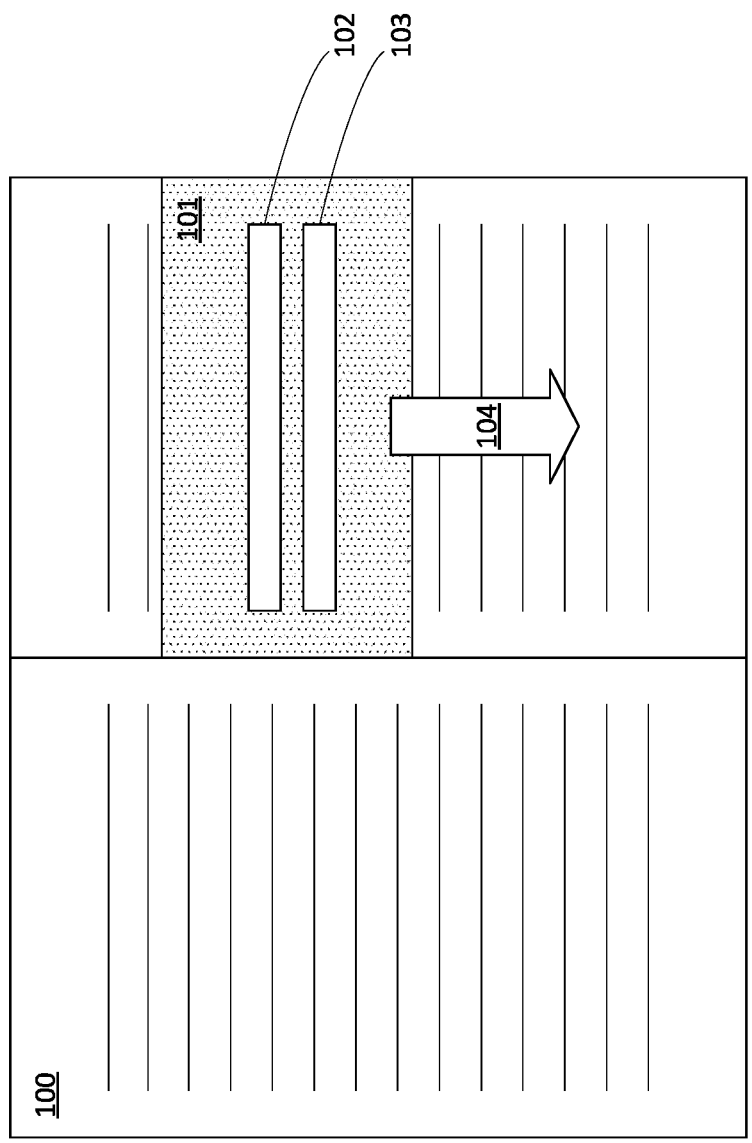
FIG. 1 illustrates a text-to-Braille device being used to read a book.

FIG. 1 illustrates an open book 100 with left and right pages showing. Each page has a single column of text, with each line of text represented by a horizontal line across the page. In front of the right page is a text-to-Braille device 101. The text-to Braille device 101 has a refreshable Braille display made up of two lines of cells: a first line 102 and a second line 103. The refreshable Braille display 101 is placed on the right page of the book 100 and converts the written text below the device 101 into Braille characters, which are displayed by the refreshable Braille display 102, 103.

The amount of written text below the text-to-Braille device 101 is greater than the amount of text in Braille that can be displayed by the two rows 102, 103 of the refreshable Braille display. The device 101 cycles through the text in the written words by outputting segments of text in turn that fit on the two rows 102, 103 of the display 101. Once all of the written text has been output via the refreshable Braille display 102, 103, then a user will move the text-to-Braille device 101 down the page as indicated by the arrow 104 to enable further text on the page to be read.

Figure 2:
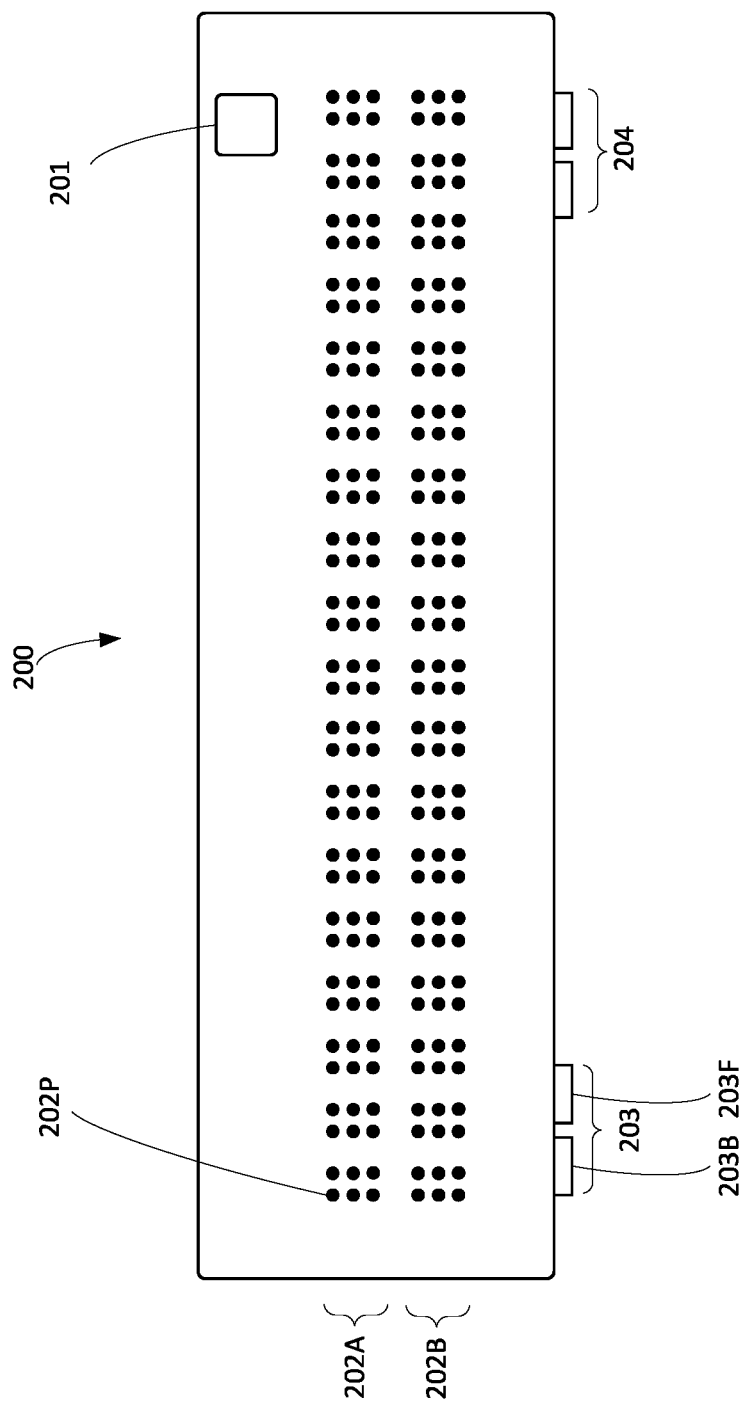
FIG. 2 illustrates a top view of a text-to-Braille device.

FIG. 2 illustrates a text-to-Braille device 200 showing a number of features visible from a top perspective. The device can be turned on and off using a power button, not visible from this perspective. An image button 201 is shown at the upper right of the device 200. The image button 201 causes an imaging operation by the device 200 to electronically capture an image of text on a page below the device 200.

A refreshable Braille display 202A, 202B spans across the device 200 and is made up of a first row 202A and a second row 202B of Braille cells. Each Braille cell is made from a collection of six pins; an individual pin from the first Braille cell of the first row 202A is labelled as "202P". FIG. 2 and the accompanying Figures illustrate two rows of six-pin Braille cells; however, the number of rows can be deceased to one or increased to more than two, and the number of pins that make each cell can be increased or decreased, for example, the current six pins enable six-dot Braille to be displayed, while an additional two dots for each cell would enable eight-dot Braille to be displayed by each cell of the first and second rows 202A, 202B. Each row 202A, 202B is made up of eighteen cells, but this number may be increased or decreased to best fit the dimensions of the device.

Two sets of panning buttons 203, 204 are shown protruding from the side of the device 202 with a left set of panning buttons 203 having a first pan button 203B and a second pan button 203F, and a right set of panning buttons 204 having a first pan button and a second pan button. The control provided by both first panning buttons and both second panning buttons is identical, so the left set of panning buttons 203 will be described in detail. Pressing of the left panning button 203B causes the text display by the refreshable Braille display to move backward and text previously displayed by the display if re-displayed, so text in Braille previously output via the first and second rows 202A, 202B can be read by a user of the device 200; and pressing of the right panning button 203F causes the text display by the refreshable Braille display to move forward, so new text in Braille output via the first and second rows 202A, 202B can be read by a user of the device 200. The configuration of the panning buttons is exemplary and may be replaced by one or more touch sensitive controls located at differing locations on the device 200.

There are a number of preferable sizes for the text-to-Braille device 200. The widths described below represent the edge-to-edge length across the device 202 in the direction along the first row of Braille cells 202A (horizontal in FIG. 2). The depths described below represent the edge-to-edge length from the side proximal to the image button 201 to the side proximal to the right set of panning buttons 204 (vertical in FIG. 2). The heights described below are not represented in FIG. 2, but would be the edge-to-edge length of the device 202 from the flat surface shown FIG. 2 to a parallel surface into the page.

In a first example, the width is approximately five inches, the depth is approximately two inches and the height is approximately one inch. This small size is optimized to be highly portable for a user.

In a second example, the width is greater or approximately equal to six inches, the depth is approximately three inches and the height is greater than or approximately equal to two inches. This larger size is optimized to be portable, like the first example, but also cover a greater area of the printed document being read.

In a third example, the width is approximately nine inches, the depth is approximately four inches and the height is greater than or approximately equal to two inches. This third example is optimized to read both standard A4 sheets and also most books.

In a fourth example, the width is approximately eleven inches, the depth is approximately six inches and the height is greater than or approximately equal to two inches. This fourth example is optimized to be able to efficiently read large books.

Figure 3:
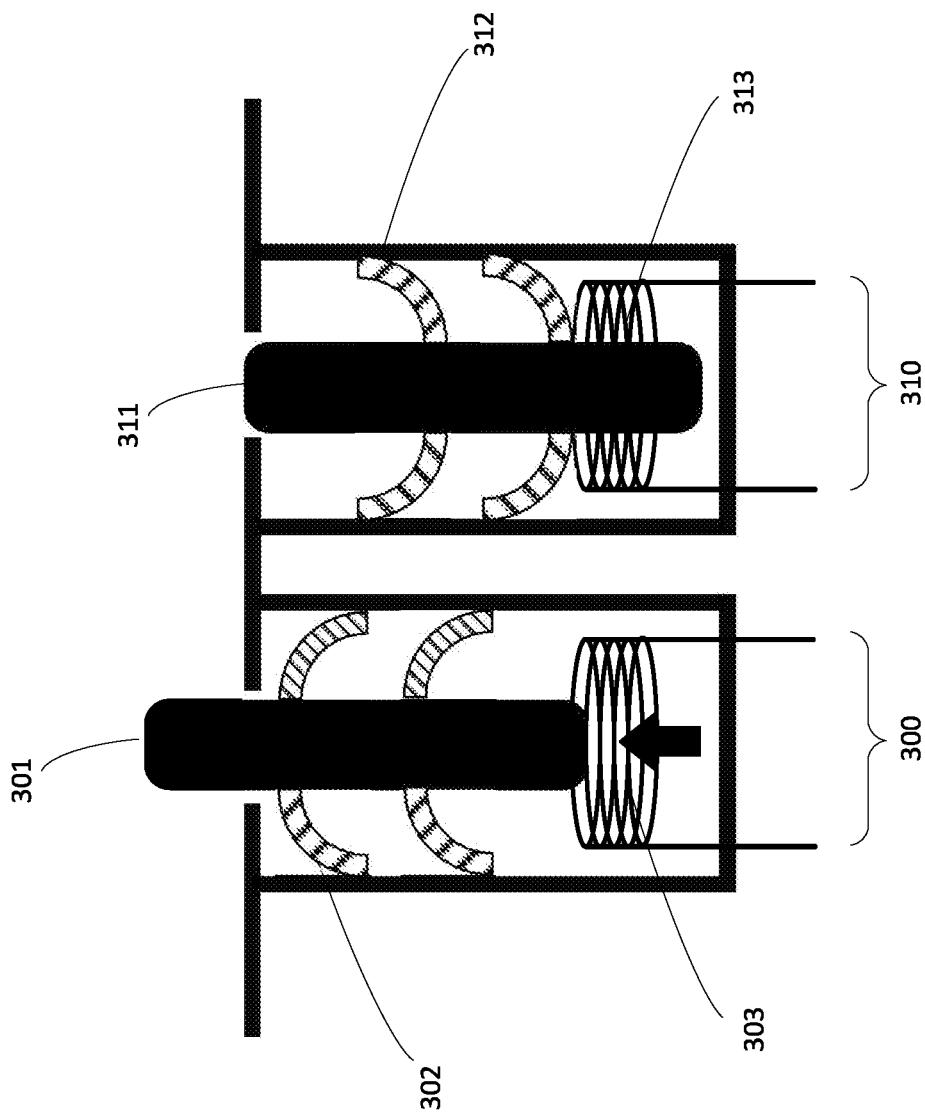
FIG. 3 illustrates a pin mechanism of a refreshable Braille display.

FIG. 3 illustrates two adjacent pins 301, 311 that form part of a Braille cell. A first pin 301 is shown in an ON position with the pin raised, and a second pin 311 is shown in an OFF position with the pin lowered. The first and second pins 301, 311 are each lineally actuated by a Lorentz force produced when current flows through a respective first or second copper coils 300, 310 in a specific direction. Each pin 301, 311 is held in place when no Lorentz force is applied by a two bi-stable hinges that surround each pin 301, 311. The bi-stable hinges form a diaphragm with the pin projecting through the center of the diaphragm. In the Figure, the first pin 301 is shown in a first position (ON position) with an upper bi-stable hinge 302 in a first position holding the first pin in said first position, and the second pin 311 is shown in a second position (OFF position) with an upper bi-stable hinge 312 in a second position holding the second pin in said second position.

In an exemplary arrangement, each pin was made to be 1.5 mm (approximately 7/128 inches) in diameter and IS mm (approximately 35/64 inches) in height. A bi-stable hinge paring as described above was able to withstand the force of the gravity acting on each pin plus an additional 0.3 Newtons of force pressing down on each pin without a continuous application of current to a corresponding magnetic coil.

A first pin option is to have a non-magnetic metallic pin. A second pin option is to have a pin made from a permanent magnet, whereby when no current is being applied through a copper coil corresponding to the pin and a user presses on the pin in an ON position with a force greater than that provided by the bi-stable hinges, the pin will move to an OFF position and as electrical current will be induced in the copper coil. This induced current can be detected by a monitoring circuit thereby detecting a user inputting information into the device by augmenting the positions of one or more pins of the device. A microcontroller or an amplification circuit connected to a microcontroller may be used to detect this pin input. A user may manually alter a number of pin states and the microcontroller may read the alterations and convert the manual Braille input into a text string.

The number of bi-stable hinges associated with each pin 301, 302 in FIG. 3 is shown as two; however, this number can be increased or decreased to alter the characteristics of the pin movement.

Alternative pin mechanisms, rather than those described above, may be substituted. An alternative mechanism is a piezoelectric cell to control each pin. Another alternative mechanism is an electroactive polymer for to control each pin. A further alternative mechanism uses a microfluidic system to control each pin. In a first example of a microfluidic system, a resistive heater heats up a small volume of liquid (less than 0.5 mL) that has a low-temperature boiling point (less than 100 degrees Celsius, equivalent to 212 degrees Fahrenheit). The liquid expands as the liquid boils and the expansion activates a latch mechanism to latch or unlatch a biased Braille pin. In a second example, a combination of micro-pumps and capillary action within tubes with a diameter of less than 1 mm (3/64 inches) that contain less than 0.5 mL of liquid create sufficient pressure to activate a latch mechanism to latch or unlatch a biased Braille pin.

Figure 4A:
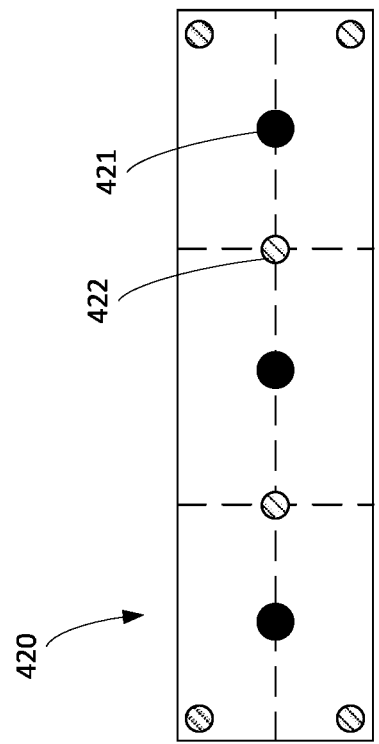
FIG. 4A illustrates a first cross-sectional view of a camera array of an imaging module of a text-to-Braille device.

FIG. 4A illustrates a cross-sectional view of an imaging module 400 for a text-to-Braille device. The front of the text-to-Braille device (proximal to the two sets of panning buttons 203, 204 in FIG. 2) would be on the left of the Figure and the rear of the text-to-Braille device (proximal to the image button 201 in FIG. 2) would be on the right of the Figure. The section passes through a camera 401 that is mounted on the roof of a recess 402 in the bottom of the imaging module 400. The cross-section of the recess 402 is shown as rectangular in the Figure, but the recess may be any other shape that does not interfere with the field of view 403 of the camera. The field of view 403 is represented by two dashed lines projecting from the camera 401. The horizontal dashed line in the Figure at the mouth of the recess 402 denotes the area of an object that is being imaged by the camera 401, such as a page being scanned by a text-to-Braille device including an imaging module 400 in accordance with that shown in the Figures. A center line projecting from the camera 401 is represented by a dot-and-dash vertical line. The angle α made between the center line of the camera 401 and a flat object at the mouth of the recess 401 is 90 degrees. The recess 402 is shown as open in the Figure; however, in an alternative example, there may be a transparent plastic plate across the recess 402 opening (along the dashed line shown in the Figure) formed from a hard plastics material, such as Perspex, or a toughened glass material.

Figure 4C:
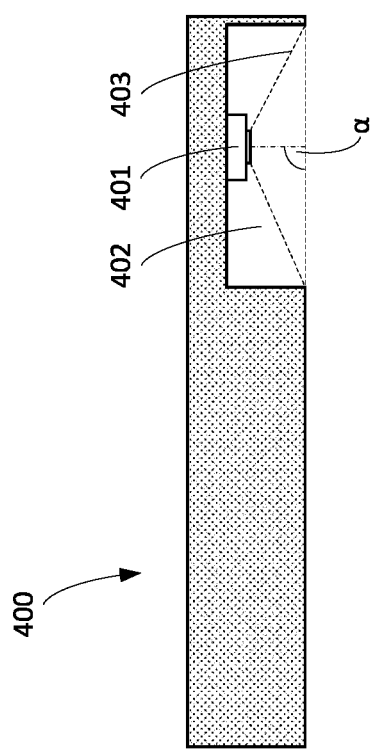
FIG. 4C illustrates an upward view of a three-camera array of an imaging module according to FIG. 4A.
Figure 4B:
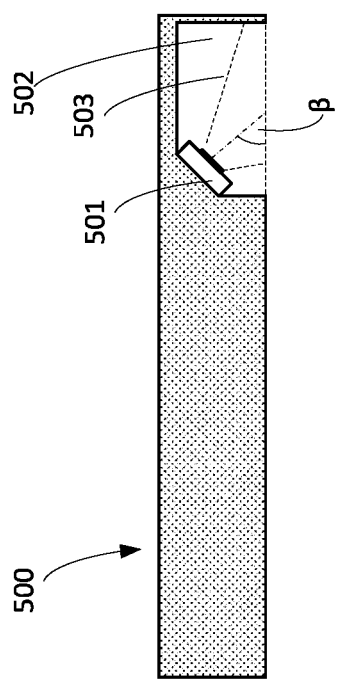
FIG. 4B illustrates an upward view of a two-camera array of an imaging module according to FIG. 4A.
Figure 6B:
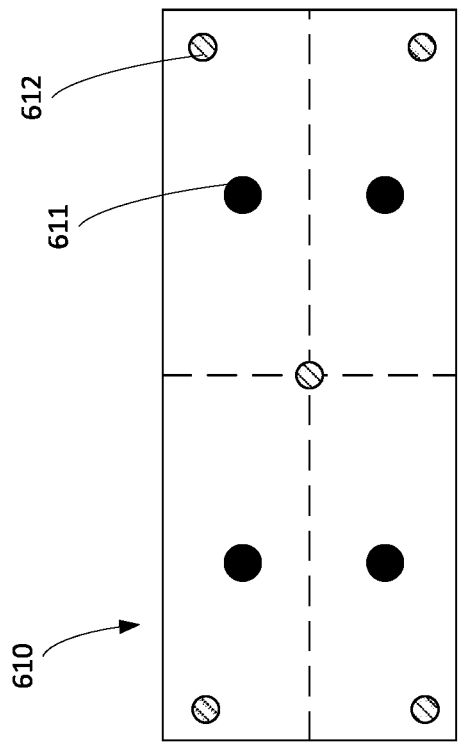
FIG. 6B illustrates an upward view of a four-camera array of an imaging module according to FIG. 6A.
Figure 6C:
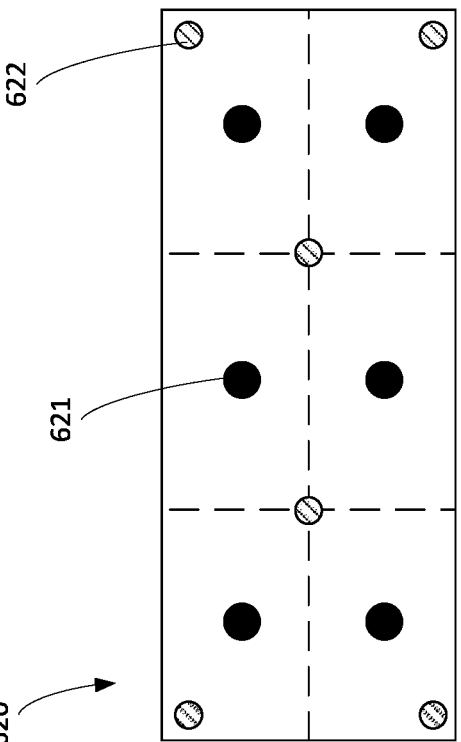
FIG. 6C illustrates an upward view of a six-camera array of an imaging module according to FIG. 6A.

FIG. 4B illustrates the underside plan view of the recess 402 opening in FIG. 4A. The recess 402 houses two equally spaced cameras 411 and also five light sources 412 that include diffusers to provide an even distribution of light emitting from each of the light sources. The light sources may be LEDs, although alternative types of light sources can be substituted. The dashed lines in FIG. 4B, as well as those in later FIGS. 4C, 6B and 6C represent lines of symmetry and are included for the benefit of a reader, they do not necessarily correspond to visible or structural features.

FIG. 4C illustrates an alternative to the arrangement of FIG. 4B. The recess of FIG. 4C houses three equally spaced LEDs 421 and six light sources 422, each with an associated diffuser.

Figure 5:
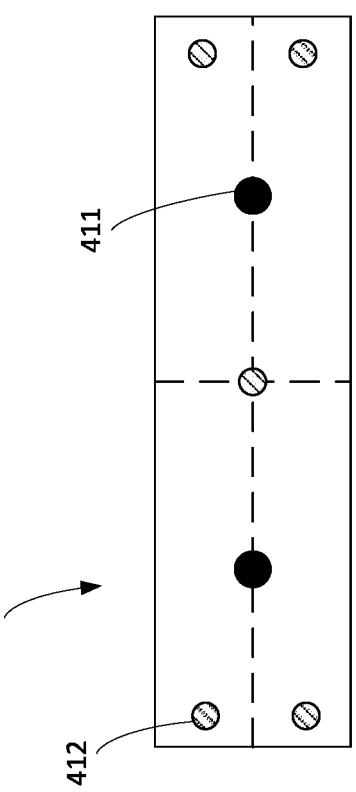
FIG. 5 illustrates a second cross sectional view of a camera array of an imaging module of a text-to-Braille device.

FIG. 5 illustrates a cross-sectional view of an imaging module 500 for a text-to-Braille device that is an alternative arrangement to that shown in FIG. 4A. In FIG. 5, the recess 502 is not rectangular and the camera 501 is mounted at an angle to the recess opening. A center line projecting from the camera 501 is represented by a dot-and-dash line. The angle β made between the center line of the camera 501 and a dashed line across the mouth of the recess 501 can be altered by changing the placement of the camera 501 within the recess 502. The angle β may be between 40 and 90 degrees, and in one example the angle is 45 degrees. The camera 501 in FIG. 5 would provide a skewed image of an object at the opening of the recess 502 due to the angle β being not equal to 90 degrees. This skew can be corrected by applying a software filter to alter an image taken by the camera 501. The angle of the camera 501 of FIG. 5 enables the use of a thinner imaging module as the camera can be placed closer to the opening of the recess 502 than the camera 401 of FIG. 4A, but at a cost to image quality.

Figure 6A:
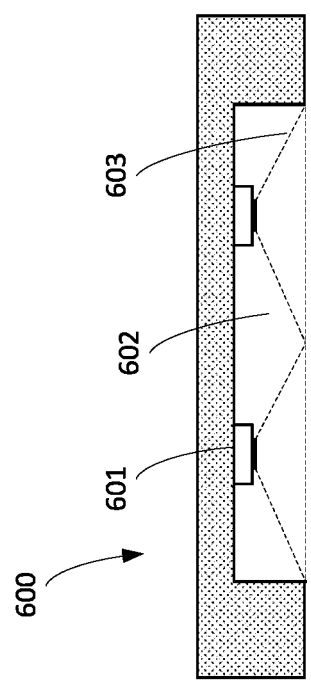
FIG. 6A illustrates a third cross sectional view of a camera array of an imaging module of a text-to-Braille device.

FIG. 6A illustrates a cross-sectional view of an imaging module 600 for a text-to-Braille device. The imaging module of FIG. 6A is an alternative arrangement to that shown in FIG. 4A. The imaging module of FIG. 6A has two rows of cameras 601 between a front and rear of the imaging module, and the section shown in the Figure passes through a camera located in each row. The two cameras 601 shown are located in a large rectangular recess 602 within the imaging module 600. As with the recess 402 of FIG. 4, the rectangular shape may be altered in any way that does not impede the field of view of the cameras 601. The field of views 603 of the two cameras 601 meet at the opening of the recess, so that a combined field including both cameras spans the opening of the recess 602. The recess 602 is shown as open in the Figure; however, in an alternative example, there may be a transparent plastic plate across the recess 602 opening (along the dashed line shown in the Figure) formed from a hard plastics material, such as Perspex, or a toughened glass material.

FIGS. 6B and 6C each illustrate an underside plan view of the recess 602 opening in FIG. 6A. FIG. 6B illustrate a recess 610 with two rows of cameras with each row having two cameras 611. There are also five light sources 612 within the recess 610 and each light source has an associated light diffuser. FIG. 6C illustrate a recess 620 with two rows of cameras and each row with three cameras 621 equally spaced. There are also six light sources 622 within the recess 620 and each light source has an associated light diffuser.

Figure 7:
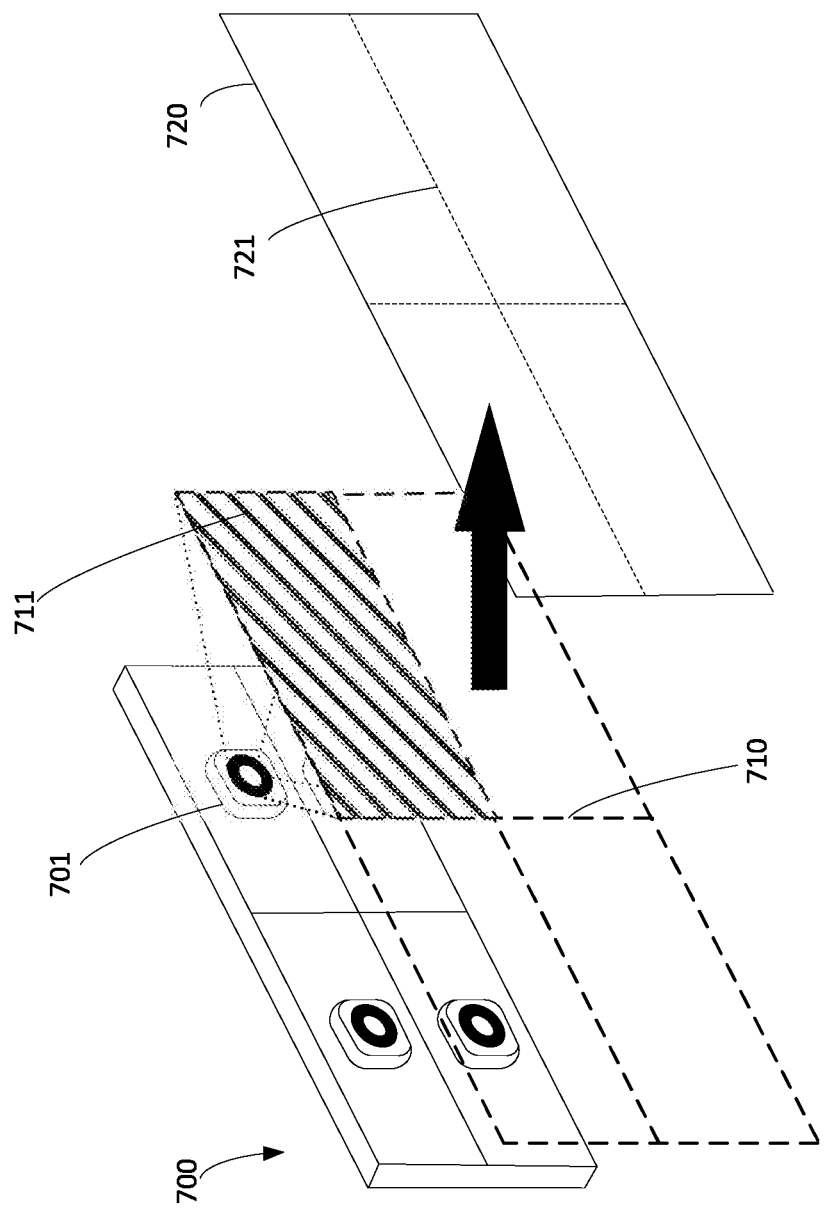
FIG. 7 illustrates an in-use imaging module of a four-camera array of an imaging module of a text-to-Braille device.

FIG. 7 illustrates an imaging module 700 of a text-to-Braille device, with the imaging module 700 comprising four-cameras 701. Each of the four cameras is operable to take an image as represented by the four rectangles in the Figure that are divided by dashed line "710". The specific camera in FIG. 7 that is labelled "701" can image the diagonal line filled area 711. The four separate images are then combined to form a single image 720 and the edges that were joined are shown by a second dashed line 721. The use of four separate cameras rather than a single camera enables an area of a plane to be imaged at a distance not possible using a single camera with the same lens.

In the above examples of Imaging Modules for text-to-Braille devices, a number of arrangements of cameras are described. A number of those examples and additional examples that provide the same beneficial effects are listed below. The plurality of cameras may form an array comprising: two cameras; three or more cameras in a straight line; three or more cameras in a straight line, wherein the cameras are equally spaced from each other; four or more cameras forming a rectangular grid; two or more parallel lines of cameras, wherein each line of cameras comprises three or more cameras in a straight line; two or more parallel lines of cameras, wherein each line of cameras comprises three or more cameras in a straight line, wherein the cameras in each line are equally spaced; or three or more regularly spaced cameras.

Figure 8:
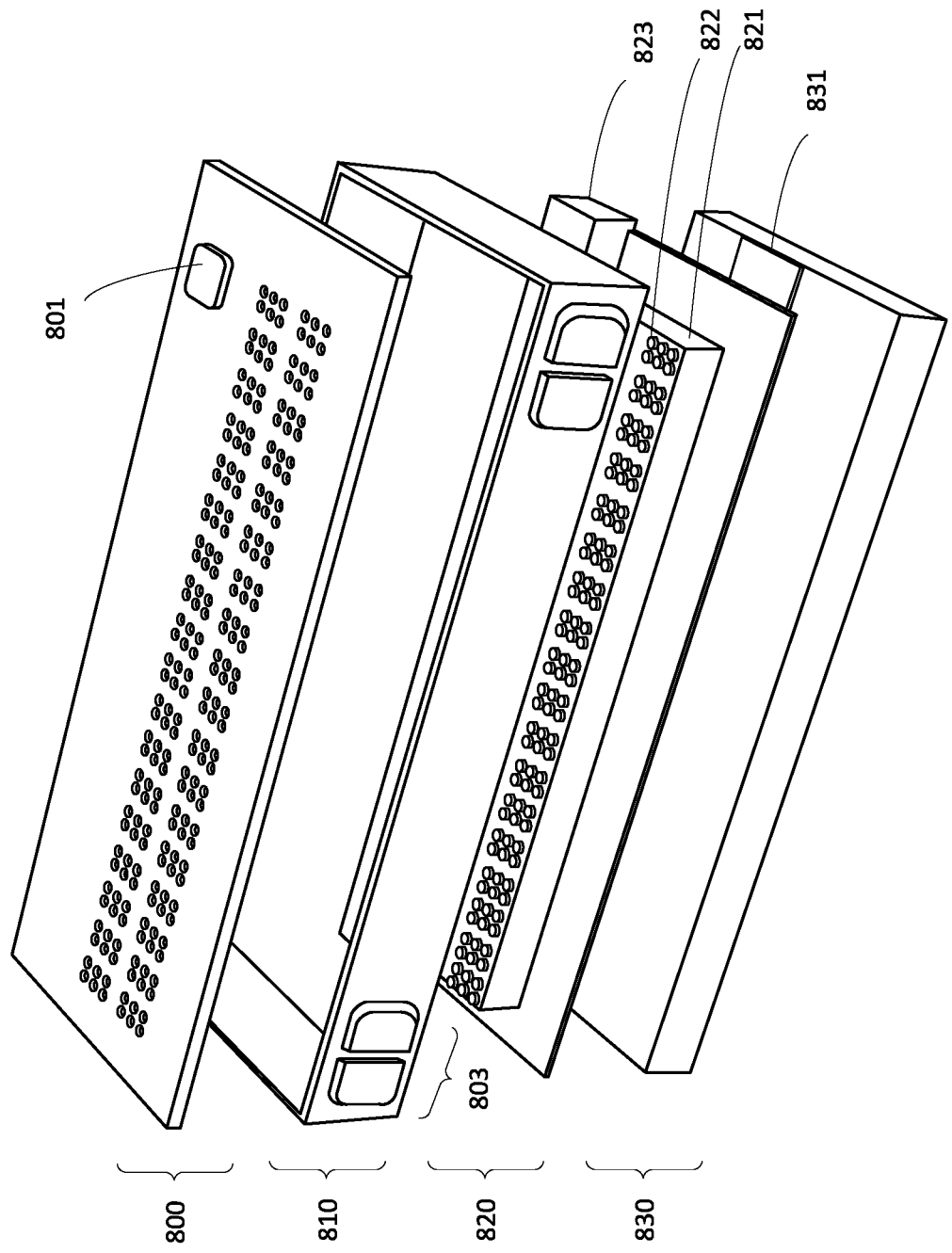
FIG. 8 illustrates an exploded view of the text-to-Braille device of FIG. 2

FIG. 8 illustrates an example exploded view of the text-to-Braille device according to FIG. 2. The device is separated into four layers 800, 810, 820, 830. The first layer 800 has two rows made up of groupings of six holes. A pin can move through each hole and each grouping of six provides a Braille cell. An image button 801 is mounted on the first layer 800. The second layer 810 comprises a rectangular case that forms the sides of the text-to-Braille device. The second layer also comprises a left set of pan buttons 803 and a right set of pan buttons all protruding from a front surface of the case, and a power button on a rear surface of the case, not shown. A third layer 820 contains the pin mechanisms 821, as described in FIG. 3, that make up each Braille cell; an individual pin is labelled as "822". The third layer 820 also contains a rechargeable battery pack 823 that can power the device. A fourth layer 830 has an imaging module according to previously described in the Figures, and also microcontroller and associated memory module 831 powered by the rechargeable battery 823. When the four layers 800, 810, 820, 830 are fitted together, the pins of the third layer can move within the holes of the first layer and project though to make a refreshable Braille display.

The case in the second layer has a micro-USB port, not shown, that is coupled to the microcontroller. Examples of devices that are suitable to provide processing power are an ARM Cortex-M4, a processor core; a ATmega328, a single chip microcontroller; a megaAVR, a single chip microcontroller; and an 8-bit tinyAVR, a very small and power-efficient single chip microcontroller.

The camera arrangements described above are positioned very close to the surface to be imaged. In some arrangements, the cameras are less than half an inch from the opening to the recess. This close proximity reduces the potential amount of text that be captured by a single camera. To increase the amount of text imaged by each camera, a wide angle lens may be installed in front of the camera or form part of the camera itself, or a system of optical lenses and a curved mirror that minify the image may be placed in front of the camera. Each of these solutions have the potential to distort the image. An additional image processing step may be required to correct or reduce the image distortion.

A number of lighting arrangements are described above. LEDs are described as being a potential light source. The lighting arrangements may generate white or monochromatic light. In testing, white light provided greatest clarity for images. Further, monochromatic lighting may obscure text written in a same or similar color, thereby reducing the accuracy of the text-to-Braille device.

Figure 9:
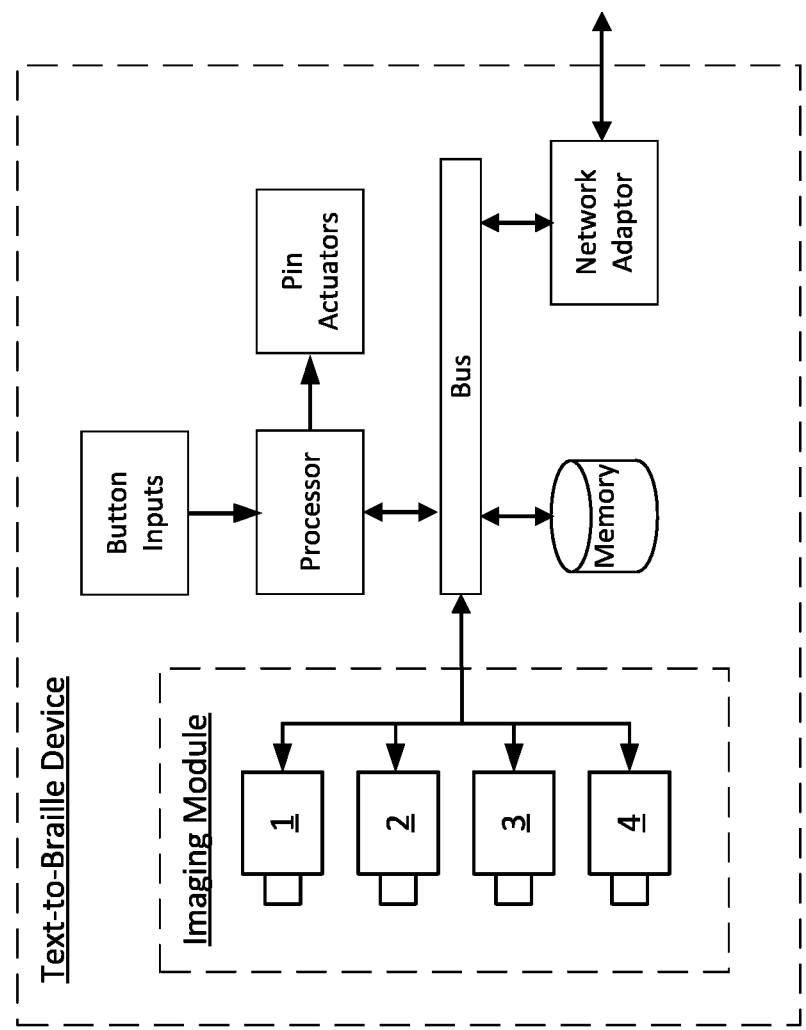
FIG. 9 illustrates a schematic diagram of a text-to-Braille device.

FIG. 9 illustrates a schematic diagram of a text-to-Braille device and includes a schematic diagram of an imaging module. The imaging module illustrated has four cameras although alternative imaging modules are described above that include fewer or more cameras. The text-to-Braille device contains a number of button inputs including an image capture button and multiple pan buttons. If any of the device buttons are pressed, the Processor detects the press signal and will take pre-programmed action. The Processor can send and receive data to and from a device Bus. The device Bus can also send and receive data with to and from a Network Adaptor, Memory and the four cameras 1,2,3,4 in the Imaging Module. The functioning of the various components in FIG. 9 will be briefly described below. A button press from the image capture button would be detected by the Processor and instruction sent to the cameras 1,2,3,4 to take an image. The four images are transmitted via the bus to the Memory where they are saved to memory. The Processor can optionally perform imaging function on the saved images, such imaging functions may be to stretch, skew, trim, stich together or apply a filter to one or more images, or any combination thereof. The processor may then instruct the transmission of image data saved in the Memory to the Network Adaptor for transmission to outside of the Device. Data can be received from outside the Device using the Network Adaptor and stored in the Memory. The Network Adaptor may be a Universal Serial Bus (USB©) port or a Wireless Local Area Network (WLAN) port according to 802.11 standards, such as a Bluetooth© wireless network adaptor. The Processor can perform an Optical Character Recognition (OCR) function on one or more images stored in the Memory to produce a text string, and convert the text string into Braille. The Braille output can then be outputted by the Processor via a serial link the Pin Actuators that move the individual physical pins on the top of the Text-to-Braille device illustrated in previous Figures and described above.

OCR can be performed using a number a publicly available methods and programs including the Microsoft Project Oxford API for OCR processing, and Tesseract, which is an open source OCR service.

Image trimming may be required if two adjoining cameras captured an overlapping image. To detect overlap specific pixels are compared from the overlapping images. An alternative method is feature-based detection, but this may not be suitable due to a lack of distinctive features in a block of text.

FIG. 9 illustrates a computing systems suitable for implementing the text-to-Braille device and associated technology disclosed herein, including any of the architectures, elements, processes, and operational scenarios and sequences illustrated in the Figures and discussed in the Technical Disclosure.

Figure 10:
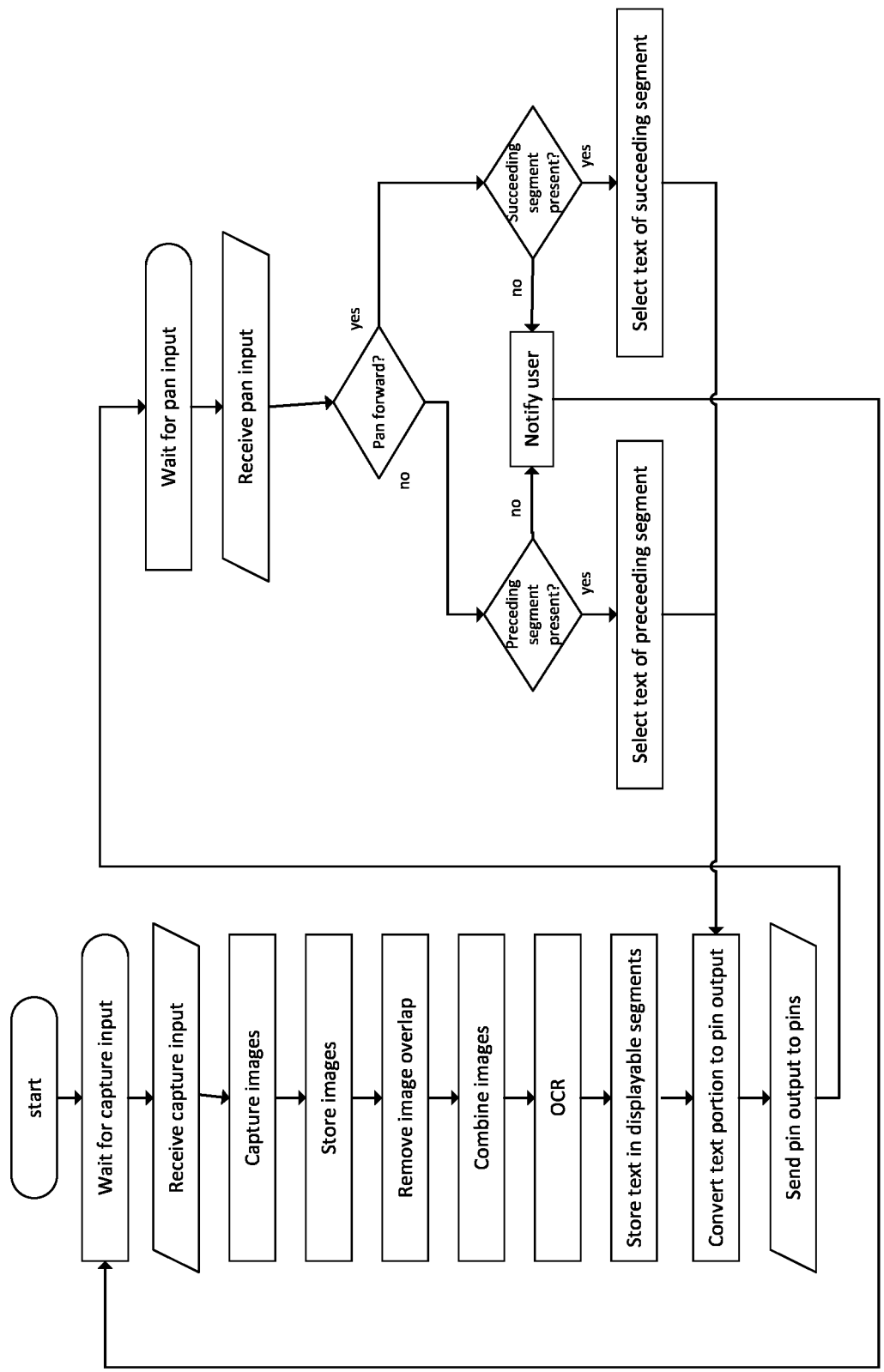
FIG. 10 illustrates a flow chart of a method for operating a Text-to-Braille device.

FIG. 10 illustrates a flow chart for a method of operating a Text-to-Braille device. The flow starts when the device is turned on or is activated and begins to wait for an input for it to capture image data. When a user presses a capture image button, the cameras each capture an image (lighting arrangements within an imaging module are activated for the capture period). The images are stored in memory on the device. Optionally, the images are processed to remove overlapping areas and are then combined into a single image. OCR is performed on the single image to generate a text string corresponding to text that was captured by the cameras in the capture image step. The text string is divided into segments of lengths that are displayable on the Braille pin output, and the first segment is transmitted to the Braille pins. The Braille pin outputs are held for a user to feel and read the displayed Braille text. The device then waits for a pan button input.

If the pan button input is to pan backward: a check is made to determine if a preceding text segment is available. If so, the preceding text segment is transmitted to the Braille pins. The Braille pin outputs are held for a user to feel and read the displayed Braille text. The device then waits for a pan button input. If a preceding text segment is not available, the user is notified, possibly by a Braille output and/or an audio cue, and the device waits for a further command for image capture for after a user has moved the device over a preceding portion of text.

If the pan button input is to pan forwards: a check is made to determine if a succeeding text segment is available. If so, the succeeding text segment is transmitted to the Braille pins. The Braille pin outputs are held for a user to feel and read the displayed Braille text. The device then waits for a pan button input. If a succeeding text segment is not available, the user is notified, possibly by a Braille output and/or an audio cue, and the device waits for a further command for image capture for after a user has moved the device over a succeeding portion of text.

The Figures and text above generally describe text performed on a Text-to-Braille device. In alternative examples, a device networked to a Text-to-Braille can optionally perform some steps mentioned above.

As described above in relation to FIG. 9, the device can include a network adaptor that can be wired (e.g. USB) or wireless (e.g. Bluetooth or Wi-Fi). The network adaptor can be used to communicate to an external device such as a portable device, such as a cell phone, or a networked computer, and possibly a server connected via the Internet.

In one example, the images taken by the device are be transmitted to a proximal cell phone using Bluetooth. The cell phone then performs the image processing steps and transmits images and/or text back to the device to be output on the refreshable Braille display, or the phone can, in turn, transmit the images to a networked computer for processing before the networked computer returns the processed images and/or text to the device via the cell phone.

In the example where a networked computer is used, the images and/or text may be stored to a network drive for later retrieval.

The functional block diagrams, operational scenarios and sequences, and flow diagrams provided in the Figures are representative of exemplary systems, environments, and methodologies for performing novel aspects of the disclosure. While, for purposes of simplicity of explanation, methods included herein may be in the form of a functional diagram, operational scenario or sequence, or flow diagram, and may be described as a series of acts, it is to be understood and appreciated that the methods are not limited by the order of acts, as some acts may, in accordance therewith, occur in a different order and/or concurrently with other acts from that shown and described herein. For example, those skilled in the art will understand and appreciate that a method could alternatively be represented as a series of interrelated states or events, such as in a state diagram. Moreover, not all acts illustrated in a methodology may be required for a novel implementation.

The descriptions and figures included herein depict specific implementations to teach those skilled in the art how to make and use the best option. For the purpose of teaching inventive principles, some conventional aspects have been simplified or omitted. Those skilled in the art will appreciate variations from these implementations that fall within the scope of the invention. Those skilled in the art will also appreciate that the features described above can be combined in various ways to form multiple implementations. As a result, the invention is not limited to the specific implementations described above, but only by the claims and their equivalents.

The invention claimed is:

1. A text-to-Braille device comprising:
   an imaging module wherein the imaging module comprises a plurality of cameras arranged within an imaging module recess of the text-to-Braille device to image capture a plurality of images of a portion of a page of text at an opening of the imaging module recess, the opening of the imaging module recess corresponding to an image plane, each of the plurality of cameras residing on a camera plane that is substantially parallel to the image plane,
   wherein each camera of the plurality of cameras has a different field of view of the image plane, and each camera of the plurality of cameras is arranged to image capture a respective part of the image plane so as to each capture at least a unique part of the page of text at the opening of the imagining module recess, each image including at least a captured overlapping portion of the image plane that is captured in at least one other image of the plurality of images;
   a processor, the processor being configured to at least control the imaging module to:
      image capture the plurality of images using the plurality of cameras,
      trim at least one of the plurality of images based on at least one captured overlapping portion, and
      after trimming the at least one of the plurality of images, join the plurality of images together to form one or more camera images; and
   a refreshable Braille display, the refreshable Braille display is operable to output Braille characters corresponding to written text present in the one or more camera images of the page of text.

2. The text-to-Braille device of claim 1, wherein the refreshable Braille display including a plurality of Braille cells, each Braille cell having a pin, a plurality of bi-stable hinges and a magnetic coil, the hinges capable of holding the respective pin in one of a plurality of positions such that the pin remains in the one of a plurality of positions without a continuous application of current to the magnetic coil.

3. The text-to-Braille device of claim 1 further comprising one or more protrusions, wherein the protrusions maintain a minimum distance between the plurality of cameras and the image plane.

4. The text-to-Braille device of claim 1, wherein the plurality of cameras point in a single direction, wherein the imaging module further comprises one or more light sources to illuminate at least a portion of the image plane.

5. The text-to-Braille device of claim 4, wherein the single direction is perpendicular to the part of the image plane.

6. The text-to-Braille device of claim 4, wherein the single direction is at an angle of between 40 degrees and 90 degrees to the part of the image plane.

7. The text-to-Braille device of claim 1 further comprising a processor, wherein the processor is operable to:
   combine the images produced by the plurality of cameras into a single image;
   perform optical character recognition on the single image to produce a string of text; and
   cause the refreshable Braille display to output at least a portion of the string of text in Braille characters.

8. The text-to-Braille device of claim 1 further comprising a processor and a network adapter, wherein the processor is operable to:
   transmit the images produced by the plurality of cameras to a remote computer using the network adaptor;
   receive a string of text from the remote computer of a further remote computer using the network adaptor; and
   cause the refreshable Braille display to output at least a portion of the string of text in Braille characters.

9. A method of converting printed text into Braille comprising:
   simultaneously capturing a plurality of images of a portion of a page of text at an opening of an imaging module recess of a text-to-Braille device, the opening of the imaging module recess corresponding to an image plane, the capturing being performed using a plurality of camera lenses arranged within the imaging module recess of the text-to-Braille device, each image including at least a captured overlapping portion of the image plane that is captured in at least one other image of the plurality of images;
   trimming at least one of the plurality of images based on at least one captured overlapping portion, and
   after trimming the at least one of the plurality of images, joining the plurality of images together to form a single image;
   performing optical character recognition on the single image to produce a string of text; and
   transmitting at least a portion of the string of text to a refreshable Braille display.

10. The method of claim 9, further comprising the steps of:
   detecting if a first captured image overlaps with second captured image; and removing the overlap from the first or second captured image prior to joining the plurality of images together to form a single image.

11. The method of claim 9, further comprising the step of applying a filter to the single image to alter the contrast ratio of the single image.

12. A system for converting printed text into Braille, comprising:

a text-to-Braille device comprising a plurality of cameras arranged within an imaging module recess of the text-to-Braille device to image capture a plurality of images of a portion of a page of text at an opening of the imaging module recess, the opening of the imaging module recess corresponding to a plane, a refreshable Braille display and a network adapter, wherein each camera of the plurality of cameras has a different field of view of the part of the plane, and each camera of the plurality of cameras is arranged to image capture a respective part of the plane so as to each capture at least a unique part of the page of text at the opening of the imagining module recess, each image including at least a captured overlapping portion of the plane that is captured in at least one other image of the plurality of images, wherein the text-to-Braille device is operable to transmit image data, via the network adapter, over a network connection; and a mobile device configured to receive image data from the text-to-Braille device over the network connection, the mobile device being physically separate from the text-to-Braille device, and wherein the mobile device is operable to trim at least one of the plurality of images based on at least one captured overlapping portion, after trimming the at least one of the plurality of images, join the plurality of images together to form one or more camera images, and perform optical character recognition (OCR) on image data to produce text data; wherein the mobile device is arranged to perform OCR on the image data received from the mobile device to produce text data, and to transmit the text data to the text-to-Braille device to be received at the text-to-Braille device using the network adapter; and the text-to-Braille device is arranged to display at least a portion of the received text at the refreshable Braille display.

13. The system according to claim 12, wherein the mobile device is further operable to combine the received images from each of the plurality of cameras into a single image prior to performing OCR on the single image.

* * * * *